United States Patent [19]

Fazakerley

[11] 3,960,659

[45] June 1, 1976

[54] TREATMENT OF PROTEINACEOUS MATERIAL

[75] Inventor: Stanley Fazakerley, Dollar, Scotland

[73] Assignee: The British Petroleum Company Limited, London, England

[22] Filed: Sept. 20, 1974

[21] Appl. No.: 507,716

[30] Foreign Application Priority Data
Sept. 26, 1973 United Kingdom............... 45099/73

[52] U.S. Cl.................................. 195/5; 195/28 R; 260/112 R; 426/656; 426/60
[51] Int. Cl.².......................................... C12B 1/00
[58] Field of Search................ 195/2, 4, 28 N, 28 R, 195/82, 65 R, 5; 260/112 R; 426/60, 204, 656

[56] References Cited
UNITED STATES PATENTS
3,809,776   5/1974   Chao............................. 195/28 N X

*Primary Examiner*—A. Louis Monacell
*Assistant Examiner*—R. B. Penland
*Attorney, Agent, or Firm*—Morgan, Finnegan, Pine, Foley & Lee

[57] ABSTRACT

The nucleic acid content of proteinaceous material in particular hydrocarbon grown yeasts can be reduced by contact with extra-cellular ribonuclease, particularly by contact with the spent aqueous medium obtained after cultivating an extra cellular ribo-nuclease producing micro-organisms in a broth comprising a carbon substrate, an aqueous nutrient medium and a gas containing free oxygen.

5 Claims, No Drawings

TREATMENT OF PROTEINACEOUS MATERIAL

The present invention relates to an enzymic process for reducing the nucleic acid content of a proteinaceous material.

In recent years a number of different proteinaceous materials have been developed for use as a substitute for the more traditional sources of protein in the diet. For example soya protein has been used increasingly as a substitute for meat. Recently attempts have been made to exploit the use of micro-organisms as a source of proteinaceous material. The whole or ruptured cells of the micro-organisms have been incorporated into animal foodstuffs as a proteinaceous material. Protein isolate, a pure form of protein derived from the whole or ruptured microbial cells has also been used for this purpose. Single cell micro-organisms for example the single cell fungi and bacteria have been the most widely used source of microbial proteinaceous material to date. Some of the more traditional single cell micro-organisms are the yeasts e.g. bakers yeast, Saccharomyces cerevisiae or the Torula yeasts. These micro-organisms are produced by fermentation processes using as the carbon substrate either carbohydrates or waste liquors from the wood or paper pulp industries. Recently fermentation processes have now been developed for converting hydrocarbons into proteinaceous materials. Such processes usually involve cultivating a single cell micro-organism in a broth comprising a hydrocarbon, e.g. a petroleum fraction as the carbon substrate, an aqueous nutrient medium and a gas containing free oxygen. The micro-organism is usually a yeast or a bacterium. Where the micro-organism is a yeast it is usually selected frm the genus Candida, e.g. *C.lipolytica* or *C.tropicalis*.

Where it is the intention to use the proteinaceous material as a foodstuff for incorporation in the human diet it is desirable that the nucleic acid content of the material should be reduced to a minimum. The reason for this is that the end point in the break-down of the purine bases in nucleic acid by the human system is uric acid. Uric acid accumulates in the body and it is thought that excess uric acid gives rise to ailments such as for example gout, and aggravates arthritic conditions.

Proteinaceous materials vary considerably in their nucleic acid content. For example ribonucleic acid content of yeast is about 8% by wt. and certain bacteria contain up to 20% of ribonucleic acid whilst liver has 2.5% by wt., meat about 2% by wt. and fish 1% by wt. ribonucleic acid content. Where it is proposed to use in the human diet substantial amounts of a high nucleic acid content proteinaceous material it is therefore desirable, if not essential, to reduce the nucleic acid content of the material before incorporating it in the food.

Chemical and enzymic processes have been proposed for reducing the nucleic content of proteinaceous material. Most chemical processes involve the use of alkalis which must subsequently be removed from the treated material before it is suitable for use as a foodstuff. Furthermore in such processes there is a considerable loss of valuable protein simultaneously with the removal of the nucleic acid. There is also a tendency for the protein which remains to be denatured. An enzymic process has been proposed wherein the proteinaceous material is subjected to an active preparation of an animal ribonuclease, in particular bovine ribonuclease. This enzymic process has an advantage over chemical processes in that the nucleic acid is attacked specifically and the remaining protein is unchanged. However the process is of academic interest owing to the high price and difficulty in obtaining a sufficient quantity of animal ribonuclease for commercial operation.

It is an object of the present invention to provide an improved enzymic process for reducing the nucleic acid content of proteinaceous material.

Accordingly the present invention is a process for reducing the nucleic acid content of a proteinaceous material which process comprises contacting the proteinaceous material in an aqueous phase with an active preparation of extra cellular microbial ribonuclease under conditions whereby the nucleic acid content of the proteinaceous material is reduced.

It is well known that micro-organisms normally produce extra cellular enzymes in any substantial quantity in response to the presence of the substrate for the enzyme. Nucleic acid is either not present at all in the medium in which micro-organisms are cultivated or is present in negligible quantities.

We have now discovered that at least certain micro-organisms are capable of producing extra cellular ribonuclease in quantities which are suitable for use in commercial enzymic processes for reducing the nucleic acid content of proteinaceous material.

It is surprising that the quantity of extra cellular ribonuclease produced in the culture medium does not inhibit growth of the micro-organism by interfering with the nucleic acid present in the cell.

It is convenient to carry out the present process in an aqueous buffer solution. Some examples of suitable buffer solutions are acetate/citrate. The pH of the reaction can be in the range 4.5 to 6.0 and is preferably in the range 5.0 to 5.5.

The temperature of the reaction can be in the range 50° to 60°C and is preferably in the range 53° to 57°C.

Most suitably the process can be conducted under conditions of mild agitation. The agitation should be sufficient to keep the proteinaceous material in suspension throughout the reaction.

Suitable contact times between the proteinaceous material and the active preparation of extra cellular microbial ribonuclease can be of the order of 30 to 120 minutes.

The proteinaceous material having a reduced nucleic acid content can be recovered from the reaction mixture by such techniques as centrifugation and spray or drum drying.

The present process is suitable for use in reducing the nucleic acid content of any of the proteinaceous materials hereinbefore described. Most suitably the proteinaceous material is a single cell micro-organism or a protein isolate derived from a micro-organism.

Preferred single cell micro-organisms are hydrocarbon utilising yeasts, in particular, hydrocarbon utilising yeasts of the genus Candida e.g. hydrocarbon utilising strains of *Candida lipolytica* and *Candida tropicalis*.

The active preparation of extra cellular microbial ribonuclease can be an aqueous broth fraction which has been obtained by cultivating an extra cellular ribonuclease producing micro-organism in a broth comprising a carbon substrate, an aqueous nutrient medium and a gas containing free oxygen.

The extra cellular ribonuclease producing micro-organism can be a hydrocarbon utilising micro-organism. We have found that, in particular, certain yeasts of the genus Candida are suitable for use as the extra cellular ribonuclease producing micro-organism. Preferred yeasts are hydrocarbon utilising strains of *Candida lipolytica* or *Candida tropicalis*. We have lodged an extra cellular ribonuclease producing hydrocarbon utilising strain of *Candida lipolytica* in the Central Bureau Voor Schimmelcultures, Baarn, Holland where it has been given the CBS number 6331.

The preferred carbon substrate is a petroleum fraction consisting of, or containing, straight chain hydrocarbons. Straight chain hydrocarbons obtained by a molecular sieve treatment of a petroleum fraction is preferred. The straight chain hydrocarbon should have at least 10 carbon atoms per molecule.

The aqueous nutrient medium can be selected from any of the media which are known to be suitable for the cultivation of the particular micro-organism. Such media usually comprise an aqueous solution of the mineral salts which are required by the micro-organism for growth.

The process can be either continuous or batch and can be carried out under aseptic or non aseptic conditions of operation.

In a preferred embodiment of the invention, the nucleic acid content of a hydrocarbon utilising extra cellular ribonuclease producing strain of a yeast grown in submerged aerobic fermentation in a broth containing the hydrocarbon, is reduced by separating the yeast from the broth e.g. by centrifugation to form a product stream of the cells of the yeast and an aqueous fraction having ribonuclease activity. The cells of the yeast are separated from the product stream as a suspension and protein is precipitated from the suspension and the precipitated protein is contacted with the aqueous fraction so as to reduce the nucleic acid content of the protein.

The nucleic acid content of the precipitated protein can be reduced by suspending it in the aqueous fraction.

Preferably the suspension of the cells of the yeast contains up to 10% by weight of the cells.

The protein is preferably precipitated from the suspension by making the suspension alkaline e.g. a pH of 9 by addition of an alkali such as sodium hydroxide and centrifuging, to form a protein containing solution, the protein is precipitated from this solution by the addition of an acid e.g. till a pH of 4 is attained. The precipitated protein can be recovered by centrifugation and drying e.g. by spray drying.

In some cases the aqueous broth fraction has sufficient ribonuclease activity for use in the present process without further treatment. This is the case, for example when the ribonuclease producing micro-organism is *Candida lipolytica* CBS number 6331. However, with other micro-organisms it may be necessary to subject the aqueous broth fraction to a treatment whereby the ribonuclease activity is increased. A suitable technique for increasing the ribonuclease concentration of the broth is ultrafiltration.

The present invention is further illustrated by but not limited to the following Examples.

EXAMPLE 1

A. Production of a Broth Fraction Having an Extra Cellular Ribonuclease Activity

*Candida lipolytica* strain CBS number 6331 was cultivated continuously under non aseptic conditions of operation in a broth comprising an aqueous nutrient medium in the presence of a kerosine boiling range n-paraffin and a gas containing free oxygen. The aqueous nutrient medium had the following composition.

| | |
|---|---|
| $H_3PO_4$ | 1.594 g. |
| KCl | 0.916 g. |
| $MgSO_4.7H_2O$ | 0.521 g. |
| $MnSO_4.4H_2O$ | 0.035 g. |
| $FeSO_4.7H_2O$ | 0.052 g. |
| $ZnSO_4.7H_2O$ | 0.153 g. |
| $CuSO_4.7H_2O$ | $4.36 \times 10^{-4}$ g. |
| $H_2SO_4$ | 0.172 g. |
| Thiamine HCl | 220 mg. |
| Tap Water to | 1 liter |

The nitrogen source was gaseous ammonia which was added separately to the broth. The fermentation pH was maintained in the range 4.0 to 5.5. The fermentation temperature was maintained in the range 27° to 33°C. The dilution rate was 0.15 liters per hour.

A product stream containing whole cells of *Candida lipolytica* was continuously recovered from the fermenter and an aqueous broth fraction was separated therefrom by centrifugation. The aqueous fraction had sufficient extra cellular activity to enable it to be used in the process of the present invention without further treatment.

B. Preparation of Proteinaceous Material For Use in the Present Process.

The whole cells of *Candida lipolytica* strain CBS 6331 present in the product stream from the fermenter herein described in paragraph A were separated therefrom as a suspension containing 10% by wt. solids.

The pH of the suspension was adjusted to 9 by the addition of sodium hydroxide, and then centrifuged. The solid residue was discarded and the protein-containing solution adjusted to a pH of 4 to precipitate the protein, which was recovered by centrifugation and spray drying.

C. Process in Accordance With the Present Invention For Reducing the Nucleic Acid Content of the Protein Obtained.

200 grams of the protein obtained in accordance with the procedure hereinbefore described under pragraph B were mixed with 1 liter of the active preparation of extra cellular microbial ribonuclease prepared in accordance with the procedure hereinbefore described under paragraph A. 1 liter of an acetate buffer was added to give the reaction mixture a pH of about 5.2. The mixture was then stirred to maintain the protein isolate in suspension and maintained at a temperature of about 50°–60°C for 60 minutes. The protein isolate having a reduced nucleic acid content was then recovered from the reaction mixture by centrifugation. The nucleic acid content of the protein isolate was tested before and after treatment by alkaline extraction followed by U.V. estimation. The nucleic acid content of the protein isolate before treatment was 10–11 percent and the nucleic acid content of the protein isolate after treatment was 4.4%.

I claim:

1. A process for reducing the nucleic acid content of a yeast grown by submerged aerated fermentation in a broth containing a hydrocarbon substrate which process comprises the steps of:

a. separating a product stream containing the grown yeast to obtain (1) a yeast cell fraction and (2) an aqueous fraction having ribo-nuclease activity,
b. precipitating protein from said yeast cell fraction and,
c. contacting said precipitated protein with said aqueous fraction of step (a) (2) at a pH of 4.5 to 6 and a temperature of 50° to 60°C. to reduce the nucleic acid content of the protein.

2. A process as claimed in claim 1 in which the yeast is a hydrocarbon utilising strain of *Candida lipolytica* or *Candida tropicalis*.

3. A process as claimed in claim 1 in which the protein is precipitated from said yeast cell fraction by rendering said yeast cell fraction alkaline, centrifuging, discarding the solid residue and acidifying the solution to precipitate the protein.

4. A process as claimed in claim 1 in which the ribo-nuclease activity of the said aqueous fraction is subjected to a treatment to increase the ribo-nuclease activity.

5. A process as claimed in claim 4 in which the said treatment is ultra-filtration.

* * * * *